(12) United States Patent
McBride et al.

(10) Patent No.: US 7,927,068 B2
(45) Date of Patent: *Apr. 19, 2011

(54) EXPANDABLE IMPELLER PUMP

(75) Inventors: Mark W. McBride, Bellefonte, PA (US); Thomas M. Mallison, State College, PA (US); Gregory P. Dillon, State College, PA (US); Robert L. Campbell, State College, PA (US); David A. Boger, Glenside, PA (US); Stephen A. Hambric, State College, PA (US); Robert F. Kunz, State College, PA (US); James P. Runt, State College, PA (US); Justin M. Walsh, Spring Mills, PA (US); Boris Leschinsky, Mahwah, NJ (US)

(73) Assignees: Thoratec Corporation, Pleasanton, CA (US); The Penn State Research Foundation, University Park, PA (US)

( * ) Notice: Subject to any disclaimer, the term of this patent is extended or adjusted under 35 U.S.C. 154(b) by 127 days.

This patent is subject to a terminal disclaimer.

(21) Appl. No.: 12/157,267

(22) Filed: Jun. 9, 2008

(65) Prior Publication Data
US 2009/0060743 A1 Mar. 5, 2009

Related U.S. Application Data

(63) Continuation of application No. 11/227,277, filed on Sep. 15, 2005, now Pat. No. 7,393,181.

(60) Provisional application No. 60/610,938, filed on Sep. 17, 2004.

(51) Int. Cl.
F04D 29/38 (2006.01)

(52) U.S. Cl. ........ 415/131; 415/200; 415/900; 416/142; 416/189; 416/198 R; 416/234; 416/241 A; 416/236 R; 416/240

(58) Field of Classification Search ............... 416/87, 416/88, 142, 240, 198 R, 189, 228, 234, 241 A, 416/236 R; 415/200, 900, 131
See application file for complete search history.

(56) References Cited

U.S. PATENT DOCUMENTS 1,902,418 A    3/1933    Pilgrim
(Continued)

FOREIGN PATENT DOCUMENTS

EP    0 364 293    4/1990
(Continued)

OTHER PUBLICATIONS

Schmitz-Rode, Thomas et al., "An Expandable Percutaneous Catheter Pump for Left Ventricular Support", Journal of the American College of Cardiology, Vo. 45, No. 11, 2005, pp. 1856-1861.

(Continued)

*Primary Examiner* — Ninh H Nguyen
(74) *Attorney, Agent, or Firm* — Knobbe, Martens, Olson & Bear LLP

(57) ABSTRACT

An impeller includes a hub, and a plurality of blades supported by the hub, the blades being arranged in at least two blade rows. The impeller has a deployed configuration in which the blades extend away from the hub, and a stored configuration in which at least one of the blades is radially compressed, for example by folding the blade towards the hub. The impeller may also have an operational configuration in which at least some of the blades are deformed from the deployed configuration upon rotation of the impeller when in the deployed configuration. The outer edge of one or more blades may have a winglet, and the base of the blades may have an associated indentation to facilitate folding of the blades.

27 Claims, 10 Drawing Sheets

U.S. PATENT DOCUMENTS

| | | |
|---|---|---|
| 2,356,659 A | 10/1942 | Aguiar |
| 2,649,052 A | 8/1953 | Weyer |
| 2,664,050 A | 12/1953 | Abresch |
| 2,684,035 A | 7/1954 | Kemp |
| 2,789,511 A | 4/1957 | Warren |
| 2,935,068 A | 5/1960 | Donaldson |
| 3,080,824 A | 3/1963 | Boyd et al. |
| 3,510,229 A | 5/1970 | Smith |
| 3,812,812 A | 5/1974 | Hurwitz |
| 3,860,968 A | 1/1975 | Shapiro |
| 4,135,253 A | 1/1979 | Reich et al. |
| 4,149,535 A | 4/1979 | Volder |
| 4,304,524 A | 12/1981 | Coxon et al. |
| 4,458,366 A | 7/1984 | MacGregor |
| 4,540,402 A | 9/1985 | Aigner |
| 4,589,822 A | 5/1986 | Clausen et al. |
| 4,625,712 A | 12/1986 | Wampler |
| 4,686,982 A | 8/1987 | Nash |
| 4,704,121 A | 11/1987 | Moise |
| 4,753,221 A | 6/1988 | Kensey et al. |
| 4,769,006 A | 9/1988 | Papantonakos |
| 4,817,586 A | 4/1989 | Wampler |
| 4,846,152 A | 7/1989 | Wampler et al. |
| 4,895,557 A | 1/1990 | Moise et al. |
| 4,900,227 A | 2/1990 | Trouplin et al. |
| 4,902,272 A | 2/1990 | Milder et al. |
| 4,908,012 A | 3/1990 | Moise et al. |
| 4,919,647 A | 4/1990 | Nash |
| 4,944,722 A | 7/1990 | Carriker et al. |
| 4,957,504 A | 9/1990 | Chardack |
| 4,964,864 A | 10/1990 | Summers et al. |
| 4,969,865 A | 11/1990 | Hwang et al. |
| 4,985,014 A | 1/1991 | Orejola |
| 4,994,017 A | 2/1991 | Yozu |
| 5,021,048 A | 6/1991 | Buckholtz |
| 5,049,134 A | 9/1991 | Golding et al. |
| 5,089,016 A | 2/1992 | Millner et al. |
| 5,092,844 A | 3/1992 | Schwartz et al. |
| 5,098,256 A | 3/1992 | Smith |
| 5,112,200 A | 5/1992 | Isaacson et al. |
| 5,112,349 A | 5/1992 | Summers et al. |
| 5,129,883 A | 7/1992 | Black |
| 5,147,186 A | 9/1992 | Buckholtz |
| 5,171,212 A | 12/1992 | Buck et al. |
| 5,201,679 A | 4/1993 | Velte, Jr. et al. |
| 5,211,546 A | 5/1993 | Isaacson et al. |
| 5,290,227 A | 3/1994 | Pasque |
| 5,300,112 A | 4/1994 | Barr |
| 5,346,458 A | 9/1994 | Affeld |
| 5,360,317 A | 11/1994 | Clausen et al. |
| 5,376,114 A | 12/1994 | Jarvik |
| 5,405,383 A | 4/1995 | Barr |
| 5,437,541 A | 8/1995 | Vainrub et al. |
| 5,458,459 A | 10/1995 | Hubbard et al. |
| 5,505,701 A | 4/1996 | Anaya Fernandez de Lomana |
| 5,527,159 A | 6/1996 | Bozeman, Jr. et al. |
| 5,533,957 A | 7/1996 | Aldea |
| 5,588,812 A | 12/1996 | Taylor et al. |
| 5,613,935 A | 3/1997 | Jarvik |
| 5,643,226 A | 7/1997 | Cosgrove et al. |
| 5,678,306 A | 10/1997 | Bozeman, Jr. et al. |
| 5,707,218 A | 1/1998 | Maher et al. |
| 5,722,930 A | 3/1998 | Larson et al. |
| 5,746,709 A | 5/1998 | Rom et al. |
| 5,749,855 A * | 5/1998 | Reitan ............... 604/151 |
| 5,755,784 A | 5/1998 | Jarvik |
| 5,814,011 A | 9/1998 | Corace |
| 5,824,070 A | 10/1998 | Jarvik |
| 5,851,174 A | 12/1998 | Jarvik et al. |
| 5,868,703 A | 2/1999 | Bertolero |
| 5,888,242 A | 3/1999 | Antaki et al. |
| 5,911,685 A | 6/1999 | Siess et al. |
| 5,921,913 A | 7/1999 | Siess |
| 5,941,813 A | 8/1999 | Sievers et al. |
| 5,951,263 A | 9/1999 | Taylor et al. |
| 5,964,694 A | 10/1999 | Siess et al. |
| 6,007,479 A | 12/1999 | Rottenberg et al. |
| 6,058,593 A | 5/2000 | Siess |
| 6,086,527 A | 7/2000 | Talpade |
| 6,123,659 A | 9/2000 | le Blanc et al. |
| 6,132,363 A | 10/2000 | Freed et al. |
| 6,135,943 A | 10/2000 | Yu et al. |
| 6,139,487 A | 10/2000 | Siess |
| 6,176,822 B1 | 1/2001 | Nix et al. |
| 6,176,848 B1 | 1/2001 | Rau et al. |
| 6,190,304 B1 | 2/2001 | Downey et al. |
| 6,200,260 B1 | 3/2001 | Bolling |
| 6,227,797 B1 | 5/2001 | Watterson et al. |
| 6,245,007 B1 | 6/2001 | Bedingham et al. |
| 6,247,892 B1 | 6/2001 | Kazatchkov et al. |
| 6,254,359 B1 | 7/2001 | Aber |
| 6,295,877 B1 | 10/2001 | Aboul-Hosn et al. |
| 6,387,037 B1 | 5/2002 | Bolling et al. |
| 6,422,990 B1 | 7/2002 | Prem |
| 6,425,007 B1 | 7/2002 | Messinger |
| 6,428,464 B1 | 8/2002 | Bolling |
| 6,447,441 B1 | 9/2002 | Yu et al. |
| 6,508,777 B1 | 1/2003 | Macoviak et al. |
| 6,508,787 B2 | 1/2003 | Erbel et al. |
| 6,517,315 B2 | 2/2003 | Belady |
| 6,532,964 B2 | 3/2003 | Aboul-Hosn et al. |
| 6,533,716 B1 * | 3/2003 | Schmitz-Rode et al. ....... 600/16 |
| 6,544,216 B1 | 4/2003 | Sammler et al. |
| 6,547,519 B2 | 4/2003 | deBlanc et al. |
| 6,609,883 B2 | 8/2003 | Woodard et al. |
| 6,610,004 B2 | 8/2003 | Viole et al. |
| 6,623,420 B2 | 9/2003 | Reich et al. |
| 6,692,318 B2 | 2/2004 | McBride |
| 6,716,189 B1 | 4/2004 | Jarvik et al. |
| 6,749,598 B1 | 6/2004 | Keren et al. |
| 6,776,578 B2 | 8/2004 | Belady |
| 6,783,328 B2 | 8/2004 | Lucke et al. |
| 6,790,171 B1 | 9/2004 | Grundeman et al. |
| 6,794,789 B2 | 9/2004 | Siess et al. |
| 6,817,836 B2 | 11/2004 | Nose et al. |
| 6,860,713 B2 | 3/2005 | Hoover |
| 6,866,625 B1 | 3/2005 | Ayre et al. |
| 6,942,611 B2 | 9/2005 | Siess |
| 6,949,066 B2 | 9/2005 | Bearnson et al. |
| 6,966,748 B2 | 11/2005 | Woodard et al. |
| 6,974,436 B1 | 12/2005 | Aboul-Hosn et al. |
| 6,981,942 B2 | 1/2006 | Khaw et al. |
| 6,984,392 B2 | 1/2006 | Bechert et al. |
| 7,010,954 B2 | 3/2006 | Siess et al. |
| 7,011,620 B1 | 3/2006 | Siess |
| 7,022,100 B1 | 4/2006 | Aboul-Hosn et al. |
| 7,027,875 B2 | 4/2006 | Siess et al. |
| 7,070,555 B2 | 7/2006 | Siess |
| 7,150,711 B2 | 12/2006 | Nusser et al. |
| 7,160,243 B2 | 1/2007 | Medvedev |
| 7,175,588 B2 | 2/2007 | Morello |
| 7,284,956 B2 | 10/2007 | Nose et al. |
| 7,331,921 B2 | 2/2008 | Viole et al. |
| 7,393,181 B2 | 7/2008 | McBride |
| 7,491,163 B2 | 2/2009 | Viole et al. |
| 7,731,675 B2 | 6/2010 | Aboul-Hosn et al. |
| 2002/0169413 A1 | 11/2002 | Keren et al. |
| 2003/0135086 A1 | 7/2003 | Khaw et al. |
| 2003/0208097 A1 | 11/2003 | Aboul-Hosn et al. |
| 2003/0231959 A1 | 12/2003 | Snider |
| 2004/0101406 A1 | 5/2004 | Hoover |
| 2005/0095124 A1 | 5/2005 | Arnold et al. |
| 2005/0165269 A9 | 7/2005 | Aboul-Hosn et al. |
| 2006/0018943 A1 | 1/2006 | Bechert et al. |
| 2006/0058869 A1 | 3/2006 | Olson et al. |
| 2007/0203442 A1 | 8/2007 | Bechert et al. |
| 2008/0103591 A1 | 5/2008 | Siess |
| 2008/0114339 A1 | 5/2008 | McBride et al. |
| 2008/0306327 A1 | 12/2008 | Shifflette |

FOREIGN PATENT DOCUMENTS

| | | |
|---|---|---|
| FR | 2267800 | 4/1974 |
| JP | H08-196624 | 8/1996 |
| WO | WO-94/05347 | 3/1994 |
| WO | WO 97/15228 | 5/1997 |
| WO | WO 99/37352 | 7/1999 |
| WO | WO-99/44651 A1 | 9/1999 |

| WO | WO 99/59652 | 11/1999 |
| WO | WO 00/12148 | 3/2000 |
| WO | WO 01/24867 | 4/2001 |
| WO | WO 03/048582 | 6/2003 |
| WO | WO-03/103745 | 12/2003 |
| WO | WO-2006/051023 A1 | 5/2006 |

OTHER PUBLICATIONS

International Search Report received in PCT Application No. PCT/US2005/33416, mailed Dec. 11, 2006, 4 pages.

International Preliminary Report on Patentability and Written Opinion of the International Searching Authority received in PCT Application No. PCT/US2005/033416, mailed Mar. 20, 2007, 7 pages.

International Search Report received in PCT Application No. PCT/US2007/07313, mailed Mar. 4, 2008, 3 pages.

International Preliminary Report on Patentability and Written Opinion of the International Searching Authority received in PCT Application No. PCT/US2007/007313, mailed Sep. 23, 2008, 6 pages.

U.S. Appl. No. 12/565,651, filed Sep. 23, 2009.

U.S. Appl. No. 12/772,810, filed May 3, 2010.

* cited by examiner

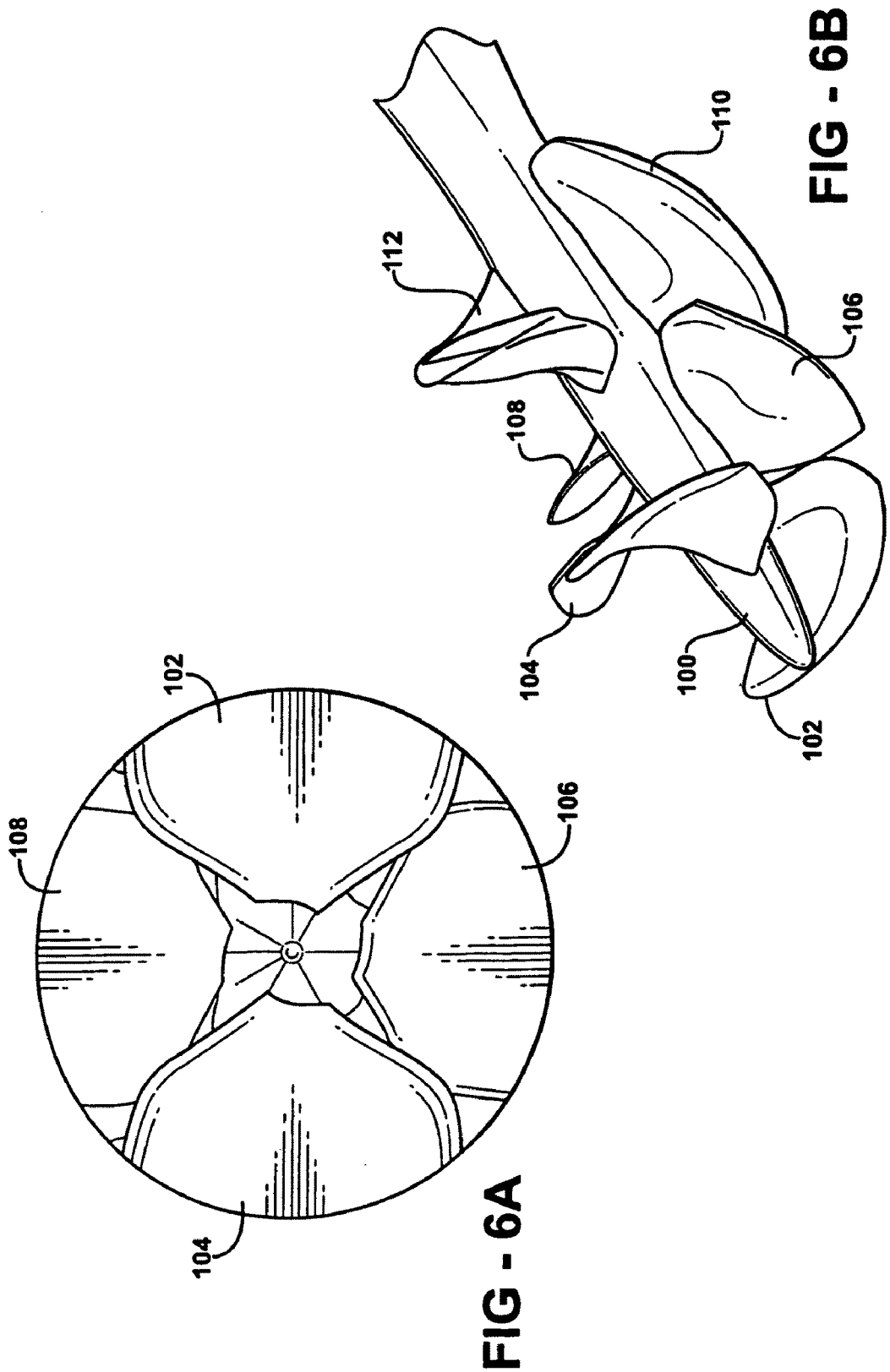

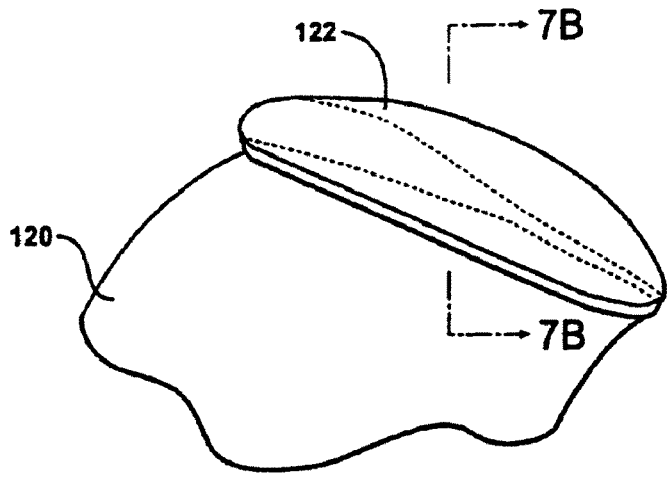
FIG - 7A
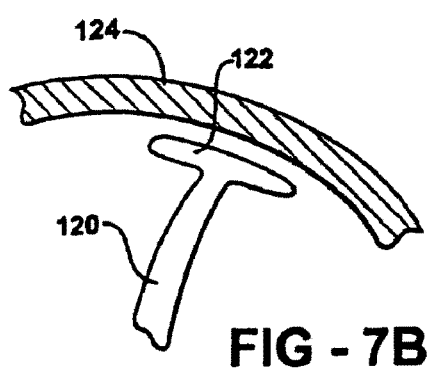
FIG - 7B
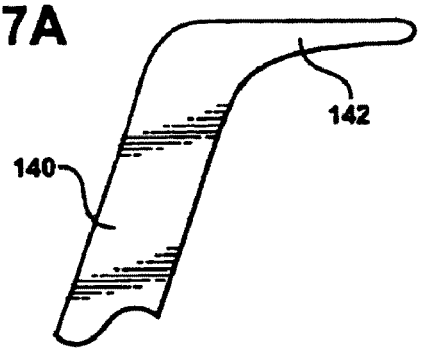
FIG - 8A
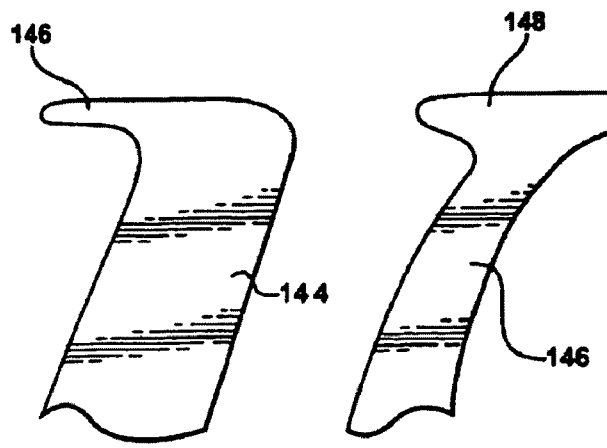
FIG - 8B     FIG - 8C
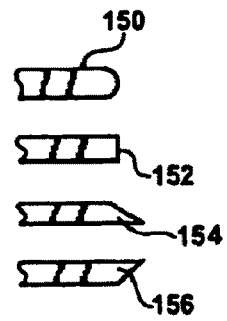
FIG - 8D

US 7,927,068 B2

EXPANDABLE IMPELLER PUMP

CROSS-REFERENCE TO RELATED APPLICATIONS

This application is a continuation of U.S. patent application Ser. No. 11/227,277, filed Sept. 15, 2005, now U.S. Pat. No. 7,393,181, which claims the benefit of the filing date of U.S. Provisional Patent Application No. 60/610,938, filed Sept. 17, 2004, the disclosures of which are hereby incorporated by reference herein.

BACKGROUND OF THE INVENTION

The present invention relates to fluid pumping impellers, in particular to expandable impellers.

Conventional impellers are manufactured with a particular blade configuration, and significant deformation of the blades is generally undesirable. Conventionally, the impeller has the same configuration during storage, movement to its operating location, and use. However, there are situations where access to the operating location is through a restricted space, or space is otherwise at a premium during storage or transport of the impeller, in which case the use of conventional impellers can be problematic.

SUMMARY OF THE INVENTION

An apparatus according to one embodiment of the present invention for inducing motion of a fluid relative to the apparatus includes an impeller. The impeller includes a hub extending in a length direction; and a plurality of blades supported by the hub, each blade having a proximal end attached to the hub and a distal end, the blades being arranged in at least two blade rows arranged in series in the length direction of the hub. The impeller has a deployed configuration and a stored configuration, each blade in the deployed configuration extending away from the hub, and at least one of the blades in the stored configuration being compressed as to move the distal end of the at least one blade towards the hub. Each blade row may include at least two blades. Furthermore, the plurality of blades may be formed integrally with the hub.

The distal end of at least one of the plurality of blades may include a winglet. In some embodiments, the distal end of each blade in at least one blade row may include a winglet. In other embodiments, the distal end of each of the plurality of blades may include a winglet.

Preferred embodiments of the present invention may further include an expandable sleeve. The sleeve may include a matrix and a film disposed around the matrix, at least part of the impeller being located within the sleeve. The matrix may be formed from a shape memory material, and the film may include an elastic polymer. The expandable sleeve may have a storage configuration and an expanded configuration. In the storage configuration, the sleeve may have a diameter less than about 4 mm. The sleeve may have an inlet end and a discharge end, with a plurality of vanes arranged at the discharge end. Each of the plurality of vanes may have an airfoil-shaped cross-section.

An apparatus according to another embodiment of the present invention for inducing motion of a fluid relative to the apparatus includes an impeller. The impeller includes a hub extending in a length direction; and a plurality of blades supported by the hub, each blade having a proximal end attached to the hub and a distal end, the blades being arranged in at least two blade rows arranged in series in the length direction of the hub. The impeller has a deployed configuration, a stored configuration, and an operational configuration. Each blade in the deployed configuration of the impeller extends away from the hub; at least one of the blades in the stored configuration of the impeller is compressed so as to move the distal end of the at least one blade towards the hub; and at least some of the blades in the operational configuration are deformed from the deployed configuration upon rotation of the impeller when in the deployed configuration.

The impeller may have a first radius in the deployed configuration and a second radius in the stored configuration which is less than half the first radius. The impeller may also have a third radius in the operational configuration, the second radius being less than half the third radius. In preferred embodiments, the impeller in the operational configuration may be operable to pump about 4 liters of fluid per minute.

BRIEF DESCRIPTION OF THE DRAWINGS

FIGS. 6A and 6B illustrate an impeller having three blade rows;

FIGS. 7A and 7B illustrate an impeller blade having a winglet;

FIGS. 8A-8C illustrate possible winglet configurations;

FIG. 8D illustrates possible winglet edge geometries;

DETAILED DESCRIPTION

Figure 1A:
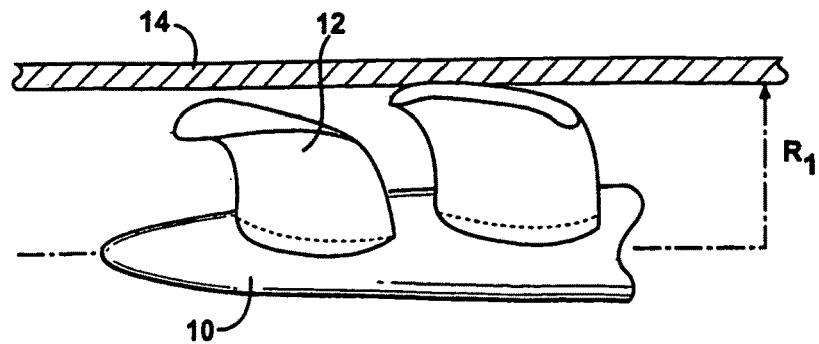
FIGS. 1A and 1B show an impeller in the deployed and stored configurations, respectively.

An impeller according to an embodiment of the present invention comprises a hub, and at least one blade supported by the hub. Embodiments of the present invention include impellers having at least one flexible blade, the impeller having a deployed configuration in which the blade extends away from the hub, and a stored configuration in which the impeller is radially compressed. For example, the blade may be folded in towards the hub, and held there by a storage sleeve such as a metal tube or cannula. In the stored configuration, the distal end of the blade is closer to the hub than in the deployed configuration, and the radius can be significantly less, such as less than half that of the radius in the deployed state. The sleeve may comprise a non-expandable portion, in which the impeller is stored, and an expandable portion, into which the impeller can be moved for deployment. The impeller deploys within the expanded portion of the sleeve.

Impellers according to the present invention may comprise a plurality of blades, arranged in blade rows. The blade rows may be spaced apart along the hub, each blade row including one or more blades. For example, each blade row may comprise two or three blades. Achieving the stored configuration is facilitated by providing multiple blade rows, rather than, for example, a single long blade curving around the hub. A single long blade can be considerably more difficult to fold in towards the hub.

Embodiments of the present invention may further include a sleeve, at least part of the impeller being located within the sleeve, and the fluid flowing through the sleeve when the impeller rotates. The sleeve may be expandable, the sleeve having an expanded configuration when the impeller is in the deployed configuration, and a stored configuration when the impeller is in the stored configuration. The sleeve may act to constrain the impeller in the stored configuration. Alternatively, a separate storage sleeve may be provided, with the impeller and expandable sleeve both expanding when pushed out of the storage sleeve. An expandable sleeve may comprise a metal framework, for example comprising a shape memory alloy. An elastic polymer film may be disposed over the metal framework. Impeller blades may have a winglet at the distal end of the blade, the winglet and the sleeve providing a hydraulic bearing for rotation of the impeller. For example, the sleeve may have a cylindrical inner surface inside which the impeller rotates, the fluid flowing through the sleeve, with the winglet of each blade moving proximate to the cylindrical inner surface as the impeller rotates, the fluid between the winglet and cylindrical inner surface forming the hydraulic bearing for rotation of the impeller.

An impeller may be stored in a storage sleeve, and deployed in a fluid pipe, through which fluid flows when the impeller is rotated. The storage sleeve may have a diameter approximately equal to or less than half the diameter of the fluid pipe. The storage sleeve may be a metal tube in which the impeller is stored prior to deployment. The fluid pipe may be a utility pipe (water, gas, sewage, and the like), bodily vessel (such as a blood vessel), portion of a thrust unit for a vehicle, or other structure through which a fluid may flow. The impeller may be conveyed to a desired location in a stored configuration, then self-deploy to an expanded, deployed state. The stored configuration facilitates conveyance of the impeller to the desired location, enabling it to be passed through openings less than the diameter of the deployed state.

The fluid pipe may be an expanded form of the storage sleeve, expansion of the storage sleeve allowing the impeller to deploy. In this case, the impeller does not need to be pushed out of the sleeve to achieve the deployed configuration. For example, an impeller according to an example of the present invention can be inserted in the stored configuration through a small entrance hole into a pipe of larger diameter. The impeller can be deployed by causing the impeller to move out of the storage sleeve using the drive shaft. The impeller then unfolds into the deployed state using stored strain energy in the blade material.

Rotation of the impeller may further change the blade configuration to an operating configuration. An impeller may have flexible blades that deform into an optimized hydrodynamic shape when rotating and operating under design load conditions.

Embodiments of the present invention include impellers having at least one blade having a winglet. In the operating state, the winglet can improve hydrodynamic performance of the impeller and reduce shear stresses that exist within the fluid. Impellers may include a plurality of blades that facilitate the folding of the blades into the storage state. The blades may be arranged in a plurality of rows of blades that facilitate the folding of the blades into the storage state, compared with folding a single blade extending a similar distance along the hub. The blades and (optionally) the hub may be constructed of a low modulus material such as a polymer. The impeller can be a unitary structure, with the blades and impeller formed from the same material, for example by molding a polymer.

An impeller with a plurality of blade rows also facilitates the input of large values of fluid head or pressure rise. The specific speed of an axial flow impeller according to the present invention may be comparable to the specific speed of mixed flow pumps.

An impeller can be inserted into a pipe in a folded state and subsequently deployed. The impeller, when deployed in a fluid flow pipe, may further deform into an operating configuration when the fluid is being pumped by impeller rotation. At the end of the operation of the impeller, the impeller can be radially compressed back into the stored configuration, for example by re-folding the flexible blades, and extracted through an entrance hole having a diameter less than that of the fluid pipe or deployed configuration. For example, the blades can be refolded and the impeller extracted into a cylindrical storage cavity by means of an attached rotary drive shaft or guide wire.

An impeller according to the present invention can operate in a low Reynolds number pipe flow, where the pipe boundary layer comprises a majority of the flow in the pipe. The Reynolds number of the relative flow over the blades can be low, compared to conventional impellers and pumps.

The impeller can be optimized to operate in a non-Newtonian fluid. The impeller can be optimized to operate in a fluid containing delicate particles (such as emulsion droplets, cells, and the like) that are damaged by excessive shearing stress in the fluid. The impeller can be designed so that the operational configuration is optimized, not necessarily the same as the deployed configuration under no loading.

An impeller with an indentation in the hub about the blade root can have reduced internal mechanical stresses within the blades when in the stored configuration. The indentation may also be used to further reduce fluid shear stress induced by the impeller in the operating state.

The blades can be formed from polymer materials, such as polyurethane. A polymer, such as polyurethane, having a modulus of 10,000 psi can be used. In some examples, the blades may have a stiffness approximating that of a thick rubber band. Hence, the blades have some stiffness but will deform under operating load. For example, the material can be chosen so as to have a linear modulus at operational stresses, allowing predictable deformation under load, and a non-linear modulus at the higher stresses used to fold the blades into the stored configuration.

FIG. 1A shows an impeller in a deployed configuration, the impeller comprising a hub 10 and blades such as blade 12. The impeller has a radius $R_1$, as measured from the central long axis of the hub to the outermost blade tip. Also shown is a fluid flow sleeve 14, through which fluid flows relative to the impeller. The impeller may be used as an axial pump, to pump fluid through the sleeve. Alternatively, the impeller may be used as a motive force provider for a vehicle. For example, the impeller may power a boat, such as a jet-boat, or other water craft, the sleeve being a tube immersed in the water surrounding the vehicle. In this configuration, the blades are deployed.

Figure 1B:
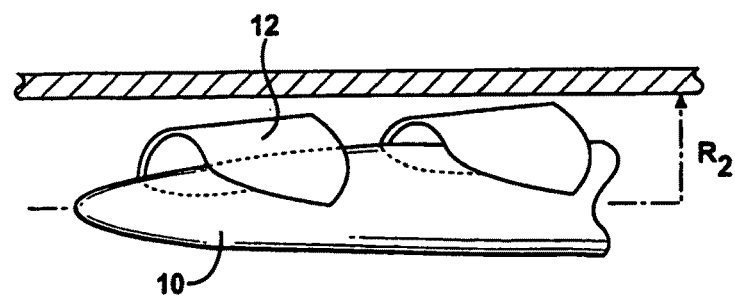

FIG. 1B shows the impeller in a stored configuration, with blade 12 folded or otherwise deformed towards the hub 10. The radius $R_2$ is less than the radius $R_1$ shown in FIG. 1A.

An impeller according to an embodiment of the present invention has flexible blades 15 that can be folded such that the maximum diameter of the impeller in the folded state is approximately half, or less than half, the diameter of the impeller in the operating state. Referring to FIGS. 1A and 1B, this corresponds to $R2 \approx \leq (R_1/2)$.

Figure 2:
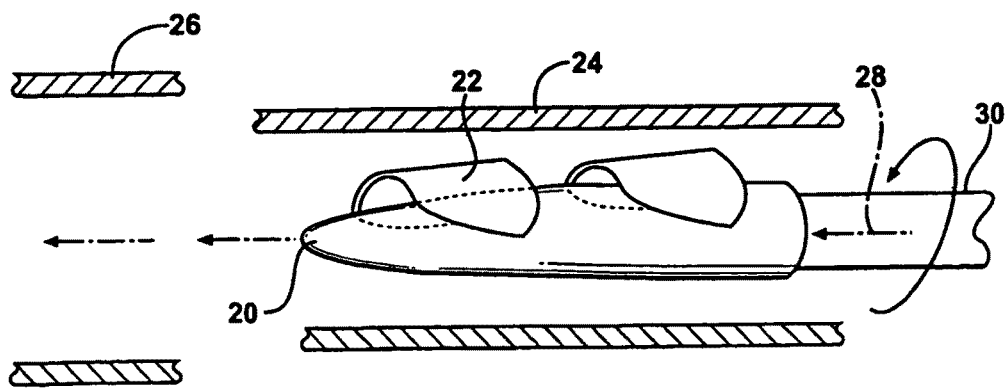
FIG. 2 schematically illustrates deployment of an impeller.

FIG. 2 is a schematic diagram illustrating deployment of the impeller. The impeller has hub 20 and blades such as 22, and is retained in the stored configuration by storage sleeve 24. A rotating shaft 30 is used to drive the impeller. The figure also shows a guide wire 28 within the rotating shaft, which can be used to position the impeller, and also to help push the impeller out of the storage sleeve. The storage sleeve may be, for example, a metal tube. Rotation of the shaft may also assist deploying the impeller, for example through twisting the impeller out of the storage sleeve if the inner surface of the storage sleeve has a threaded texture. On the left, a fluid pipe 26 is shown, through which fluid flows when the impeller is deployed and rotated.

An impeller in the stored configuration can be stored in a cylindrical cavity formed by storage sleeve 24 of diameter approximately equal to or less than half the diameter of the fluid pipe 26.

The storage sleeve may be a metal tube in which the impeller is stored prior to deployment. The fluid pipe 26 is any structure through which a fluid may flow relative to the impeller, such as a tube or bodily vessel. The impeller may be conveyed to the desired location within the fluid pipe in the stored configuration, then self-deploy to an expanded, deployed state. The stored configuration allows the impeller to pass through openings having an area less than the area of the deployed state, as swept out by the rotating blades.

Alternatively, the fluid pipe 26 may be an expanded form of the storage sleeve 24, expansion of the constraining sleeve allowing the impeller to deploy. In this case, the impeller does not need to be pushed out of the sleeve to achieve the deployed configuration. For example, an impeller can be inserted into a fluid pipe through a smaller hole, such as a smaller branch pipe or hole in the pipe wall. The impeller can then be deployed by causing the impeller to move out of the storage sleeve using the drive shaft. Deployment may occur without any outside energy input, using stored strain energy in the blades when the blades are in the stored configuration.

Figure 3:
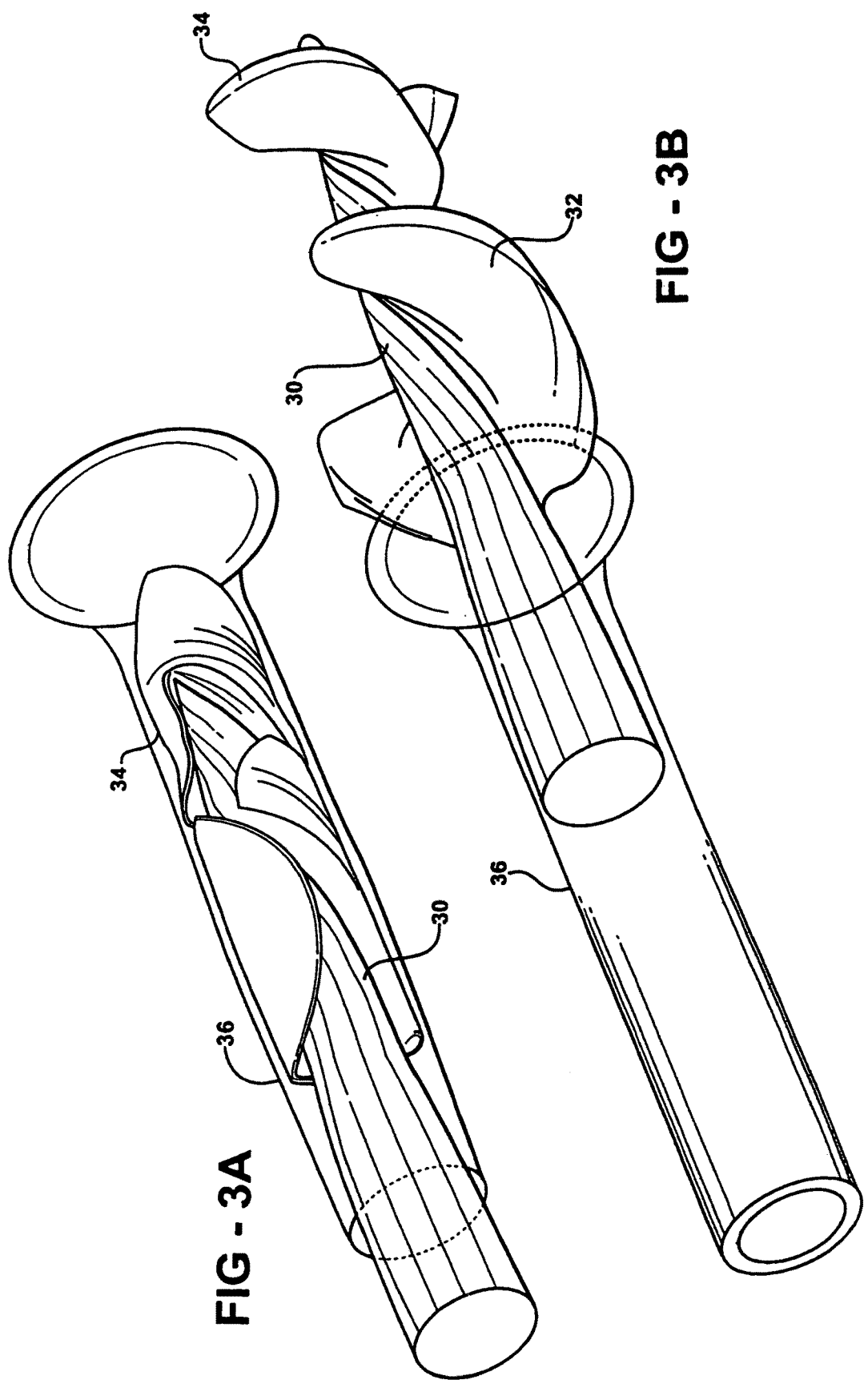
FIG. 3A illustrates an impeller in a stored configuration, within a storage sleeve.
FIG. 3B illustrates an impeller self-deploying after emerging from a storage sleeve.

FIG. 3A further illustrates an impeller in a stored configuration, showing blades such as blade 34, and hub 30. The blades are kept folded against the hub by the storage sleeve 36. FIG. 3B shows the impeller pushed out of the storage sleeve and self-deployed. The impeller has two rows of blades, as is seen more clearly in the deployed state, the first row including blade 34 and the second row including blade 32.

Figure 4:
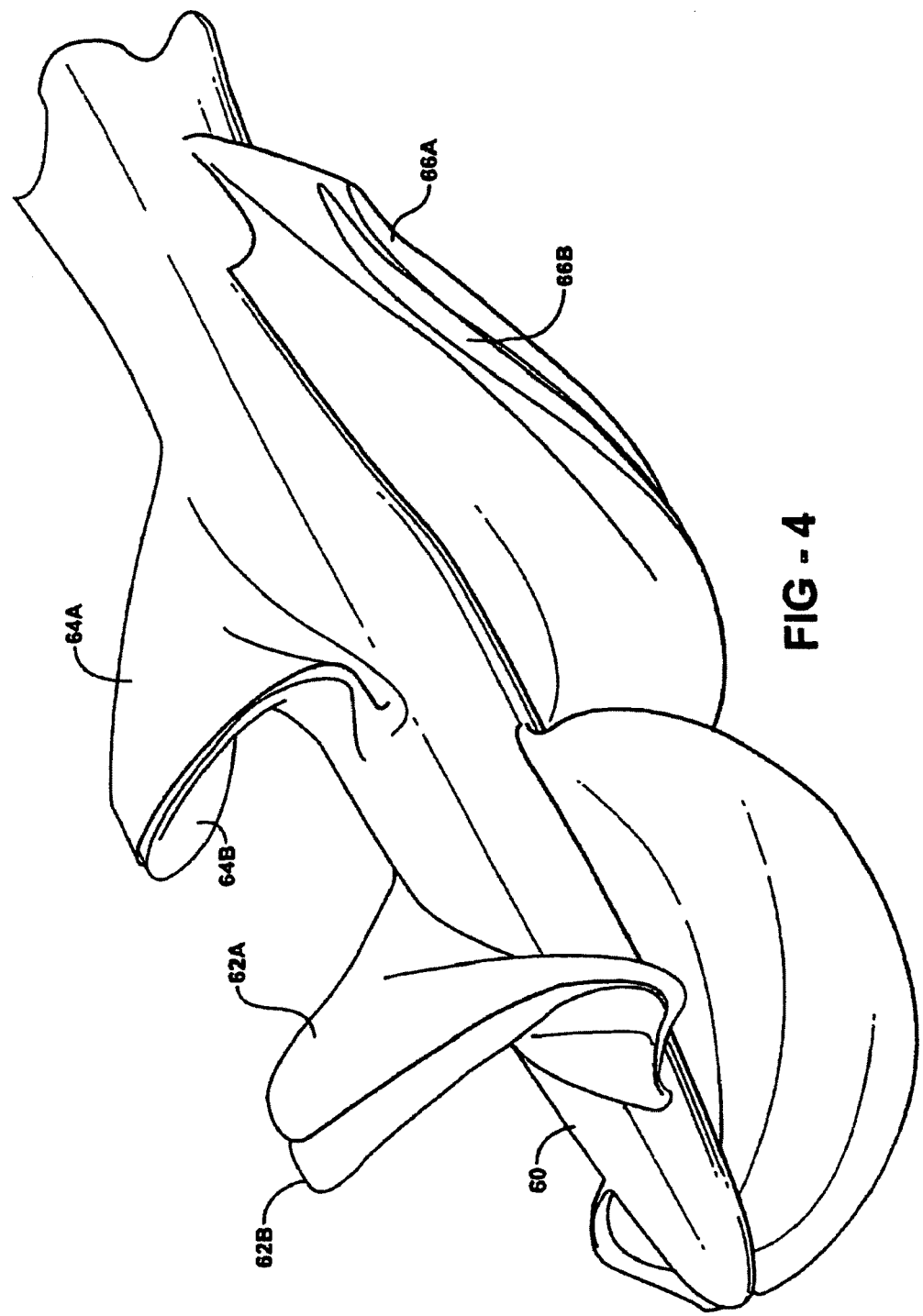
FIG. 4 illustrates deployed and operational configurations of an impeller.

FIG. 4 shows an impeller comprising hub 60 and a plurality of blades, the blades being shown in both the deployed and operating configurations. The deployed configuration is the blade configuration under no load, and the operating configuration is the configuration when the impeller rotates at the operational rotation speed. The blades are shown at 62A, 64A, and 66A for the deployed configuration. When under load, such as rotating in a fluid, the blades deform to an operational configuration, with the blades at 62B, 64B, and 66B. Rotation of the impeller changes the blade configuration from the deployed configuration (for no load) to an operating configuration. The flexible blades can deform into an optimized hydrodynamic shape when rotating and operating under design load conditions.

FIG. 4 compares the deployed blade shape with the operating blade shape. For a hub and blades formed from the same polymer, simulations showed that the hub also deflects slightly in a rotational manner, as the second blade row is rotated at the root compared to the first blade row. In general, the blades deflect forward as the lift on the blades is such that they create thrust, a force directed towards the left side of the figure, moving the blades toward the right side of the picture. The leading edge of the second blade row is obscured. There are two blade rows, each with two identical blades.

Blade shapes can be optimized using standard computational fluid dynamics analysis (CFD). However, conventionally, the non-rotating, non-loaded configuration is optimized. (If the impeller is not expandable, the deployed shape is the shape of the impeller when not rotating, and there is no stored configuration). An improved impeller has an optimized operational configuration, and an improved method of designing an impeller includes optimizing the operational configuration. A structural computation determines an allowance for deformation under load from the deployed state.

Figure 5:
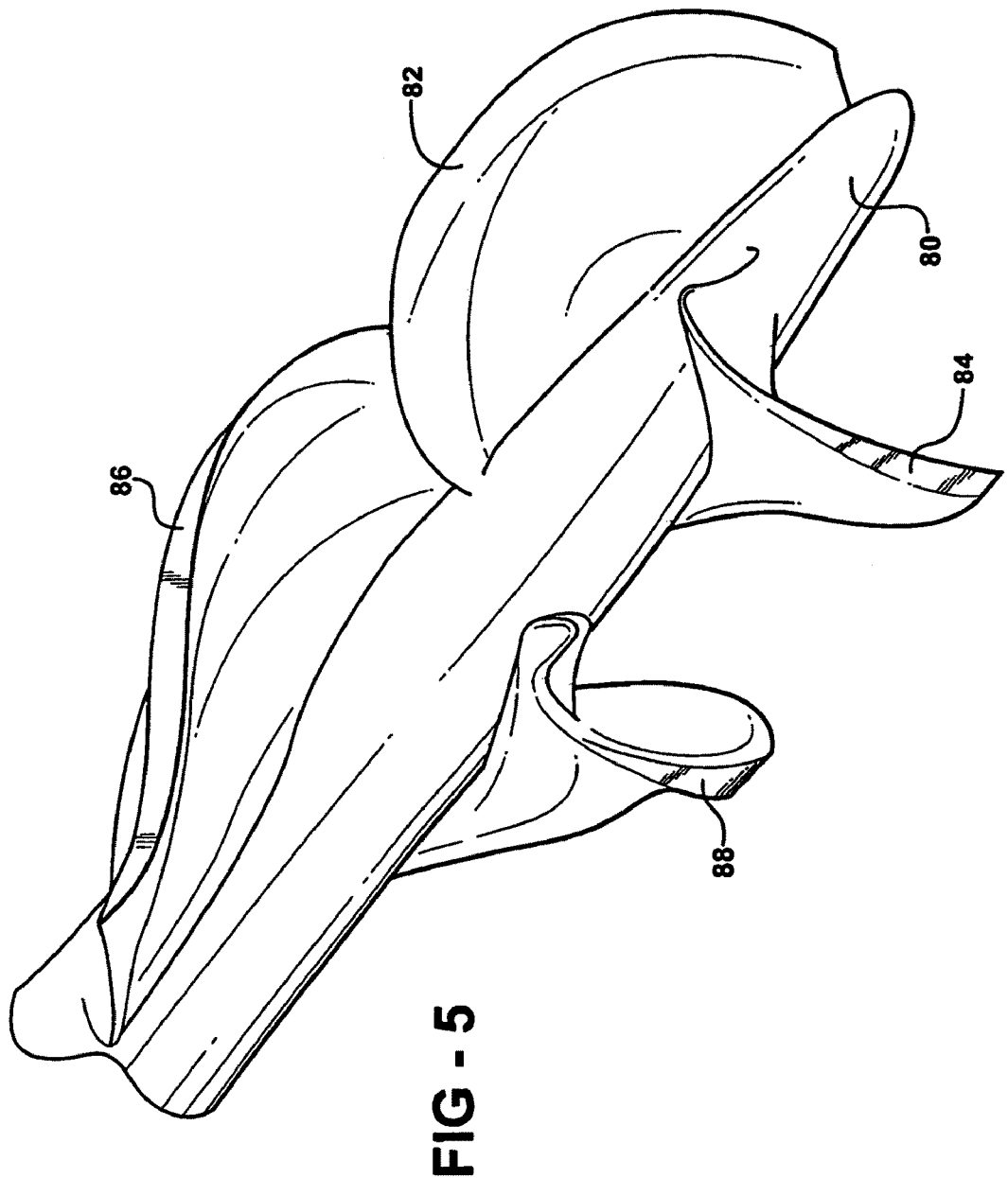
FIG. 5 illustrates an impeller design having a low Reynolds number.

FIG. 5 illustrates an impeller design having a low Reynolds number. The impeller comprises hub 80, and two rows of blades having two blades each. The first row includes blades 82 and 84, and the second row includes blades 86 and 88.

This illustration shows the design elements of a low Reynolds number impeller, where the thickness of the boundary layer on the fluid pipe walls is as thick as the diameter of the pipe. The impeller has highly curved leading and trailing edge lines where the blade pitch angles are adjusted for the local values of relative flow angle. The second row blades have a groove-like feature that takes a helical path from the leading edge to the trailing edge. This is due to variations in the spanwise loading, and allows an axial flow pump using this impeller to achieve a head rise similar to that of a mixed flow pump. The middle of the span of the blade is relatively highly loaded, leading to this feature. The second row blades may be further split into two separated blade rows, and this general feature will still present but not so apparent.

FIGS. 6A and 6B illustrate end and side views of an impeller, respectively. The impeller comprises hub 100, a first row of blades comprising blades 102 and 104, a second row of blades comprising blades 106 and 108, and a third row of blades comprising blades 110 and 112.

For a mixed flow impeller of similar performance, the hub diameter is typically much larger, so that folding into a stored diameter half the deployed diameter is impossible.

FIGS. 7A and 7B show side and end views of a blade 120 having a winglet 122 at the distal end. FIG. 7A shows the distal cross-section of the blade as a dashed line. FIG. 7B shows the winglet moving proximate to the inner surface of a fluid flow sleeve, a configuration which may be used as a hydraulic bearing for the impeller.

Impellers may have at least one blade having a winglet. In some embodiments, all blades within a blade row include a winglet; other blades may or may not have a winglet. A winglet can improve hydrodynamic performance of the impeller. A winglet may also reduce shear stresses that exist within the fluid, for example reducing degradation of biological structures such as cells that may exist within the fluid.

FIGS. 8A-8C show possible winglet configurations. An impeller blade typically has a pair of opposed faces: a pressure face inducing relative motion of the fluid through pressure as the blade rotates through the fluid; and a suction face inducing fluid motion by suction. The blade also has a leading edge cutting though the fluid as the blade rotates, a trailing edge, and an outer edge (which may also be referred to as a blade tip or edge of the distal end of the blade). The winglet is supported by the outer edge or blade tip, which has an airfoil shape. As shown, the suction side of the blade is on the right, and the pressure side is on the left.

FIG. 8A shows a suction side winglet, the winglet 142 extending from the suction side of the outer edge of blade 140. This is a view from the leading edge, in cross-section, so that the blade rotates towards the direction of viewing. FIG. 8B shows a pressure side winglet 146, extending from the pressure face of the blade 144. The parameters may be similar to the suction side winglet. The function of the pressure side winglet is to reduce flow through the gap. There is less effect of creating a hydrodynamic bearing, but the pressure side winglet "scrapes" low momentum fluid off the inner surface of the fluid pipe and prevents this fluid from entering the gap and subsequently being used in the core of a tip vortex. This can reduce shearing stresses in the bulk of the fluid flow.

FIG. 8C illustrates a combined winglet, extending from both the pressure and suction sides of the outer edge. Embodiments of the present invention include the configurations shown in FIGS. 8A-8C. Numerical methods can be used to design the winglet configurations. Where the blade chord lengths are long and the blade has a significant helical extent, the geometry and shape of the blade tip and the winglet can become complex.

FIG. 8D shows possible winglet edge geometries which may be used. The figure shows a radius edge 150, sharp edge 152, and chisel edges 154 and 156.

Figure 9B:
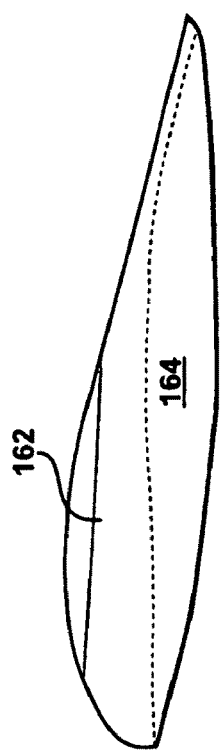
FIGS. 9A-9D illustrate an end view of an impeller blade, further illustrating possible winglet configurations.
Figure 9D:
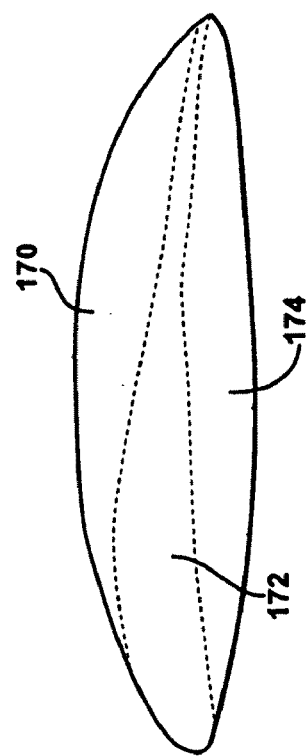
Figure 9A:
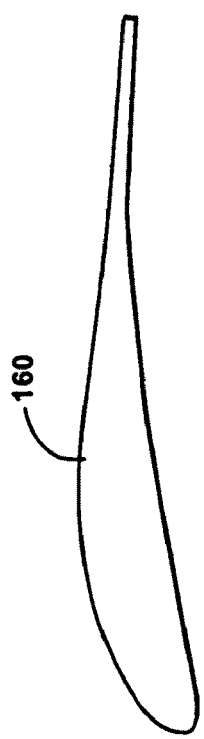

FIGS. 9A-9D further illustrate winglet configurations, the blade supporting the winglet retaining the same shape in these examples. FIG. 9A illustrates the outer edge of a blade 160, not having a winglet.

FIG. 9B shows a pressure side winglet extending the pressure side of the outer blade edge, extending over portion 164. The portion 162 of the winglet corresponds to the original outer edge area of the blade shown in FIG. 9A.

Figure 9C:
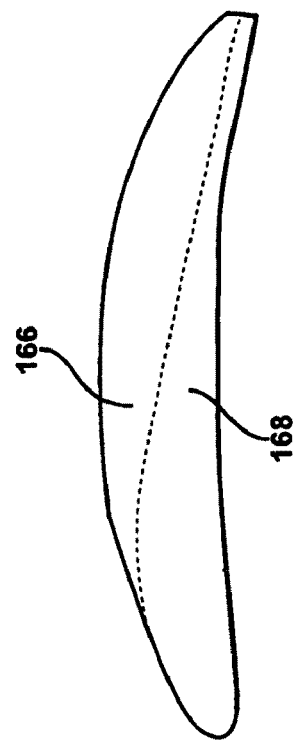

FIG. 9C shows a suction side winglet, the portion 166 extending from the suction side of the outer edge of the blade, and the portion 168 corresponding to the original outer edge of the blade. In embodiments of the present invention, the pressure side of the blade will have a radius of approximately ⅓ to ½ the blade thickness or width. The extent of the winglet may be from ½ to 3 times the blade thickness. A thickness approximately equal to the blade thickness is shown. The winglet is mostly positioned to the downstream half of the blade as shown. The purpose is to create a hydrodynamic bearing where the outer face of the winglet is in close proximity to the inner surface of the fluid pipe in which the blade is operating. Flow in the gap is reduced in strength, and a tip vortex is less likely to form. This reduces shearing stresses in the fluid. The gap can be between approximately 10 to approximately 25 percent of the base blade maximum thickness. The gap is a mostly parallel surface to the pipe of casing. It can be a cylindrical, conical, or curved side cylinder where the radius is a function of the axial position of the blade element. Parameters for the pressure side and combined (described below) winglets may be similar.

FIG. 9D shows a combined pressure side and suction side winglet extending from both the pressure face and the suction face of the blade, the portion 170 extending from the pressure face, the portion 174 extending from the suction face, and a portion 172 corresponding to the original outer edge of the blade.

The winglets are preferably aerodynamically smooth shapes. The winglets have leading edges where flows impact the edges of the winglets, and trailing edges where flow is discharged from the winglet surfaces. Winglets preferably have smooth aerodynamic cross-sections, generally in the direction of the mean flow, which is parallel to the flow direction along the blade tip surfaces.

Figure 10A:
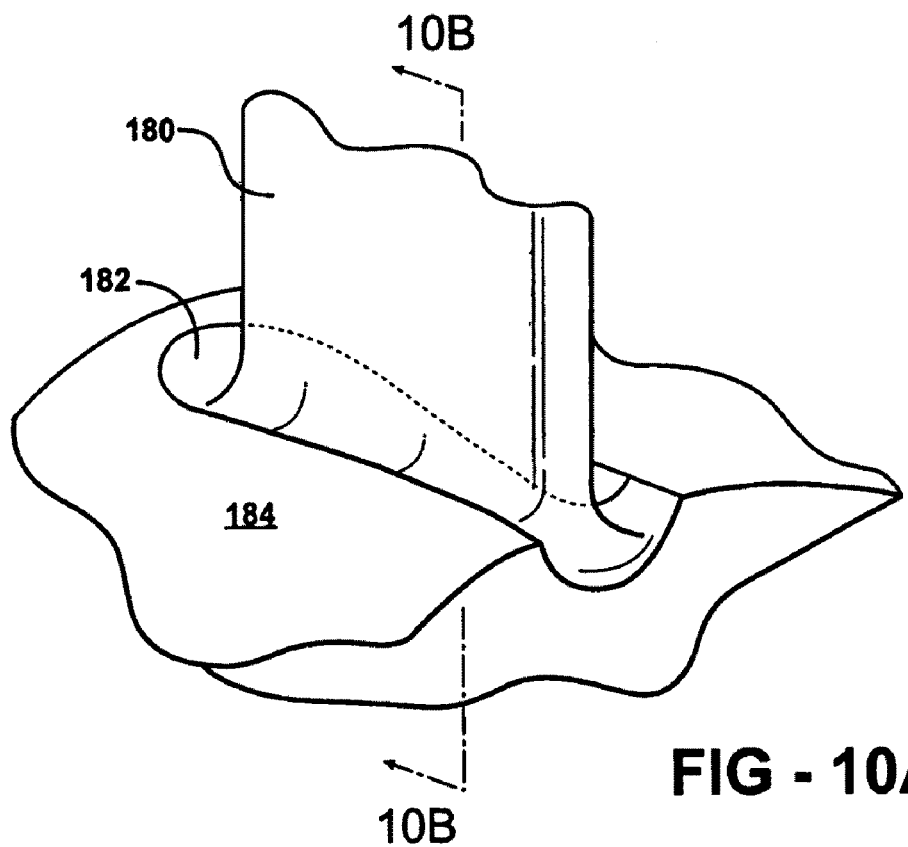
FIGS. 10A and 10B illustrate a blade having a trench around the proximate end of the blade.
Figure 10B:
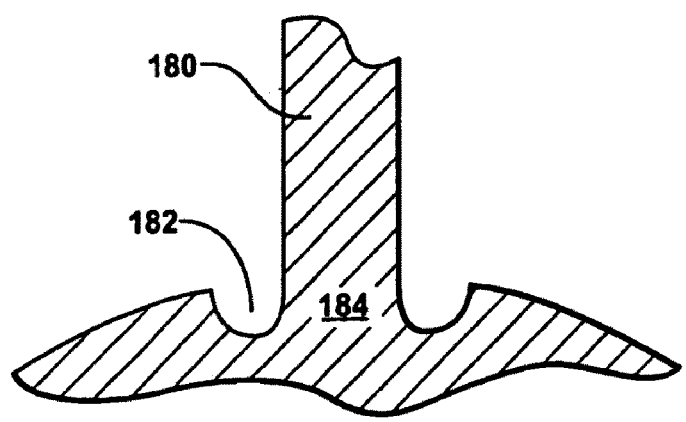

FIGS. 10A and 10B illustrate the provision of an indentation, in this case a trench, proximate to the base of a blade. FIG. 10A shows blade 180, surrounded by trench 182. The trench is formed in hub 184, and is parallel with and adjacent to the proximal edge of the blade, the proximal edge of the blade extending around the base of the blade where it joins the hub. FIG. 10B is a sectional view, showing the trench 182 and blade 180. The indentation may also be referred to as a "dillet".

An indentation close to the blade root, such as a trench around some or all of the blade root, can help reduce internal mechanical stresses in the blades when the blades are in the stored configuration, for example folded against the hub. The indentation may also be used to reduce fluid shear stress in the operating state.

Figure 11:
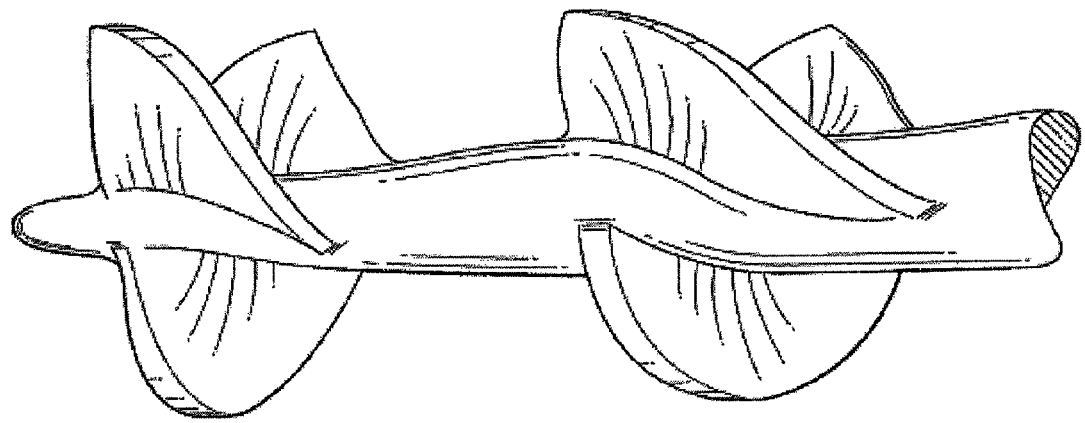
FIG. 11 illustrates a molded polymer impeller.

FIG. 11 is a photograph of an impeller molded to a configuration according to an embodiment of the present invention. The impeller is a polyurethane impeller taken from a mold, having two blades rows of three blades each.

Figure 12:
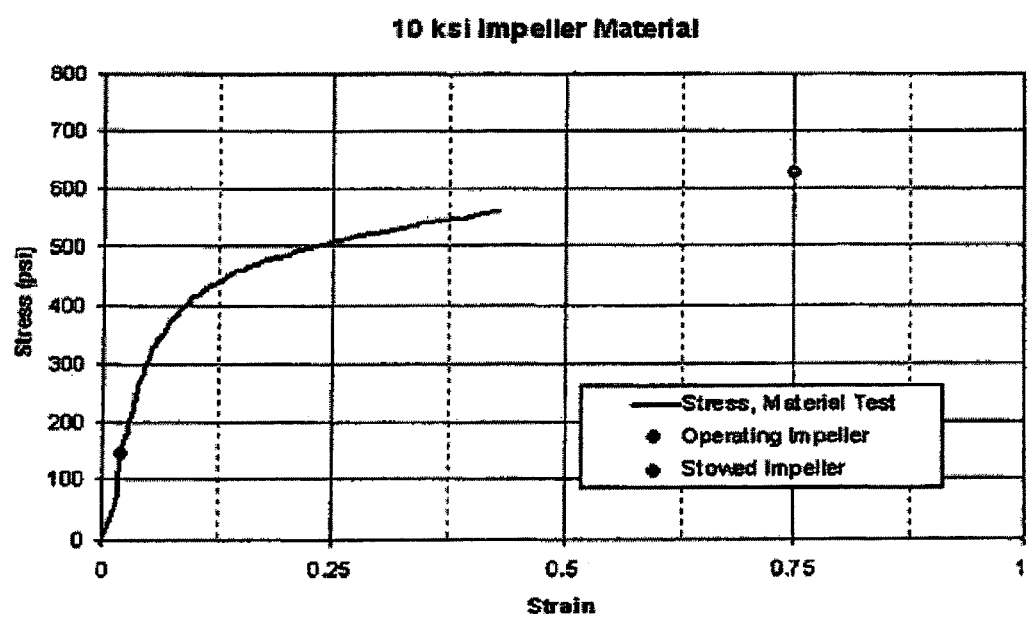
FIG. 12 shows a stress-strain curve for an impeller blade material.

FIG. 12 is a stress-strain relationship of a non-linear material that can be used to form an impeller according to the present invention. The left (low stress) and right (high stress) filled circles correspond to the impeller operating point and storage conditions, respectively. The stress/strain relationship is approximately linear at the impeller operating point. The storage condition, where the blades are folded against the hub, is within the high strain non-linear portion of the material property curve. This allows the stored configuration to be achieved without passing the material tensile failure point. In example impellers, the maximum material elongation in the stored configuration is approximately 75 percent.

Preferably, a non-linear property material is used for the blades. The blade material can be relatively stiff at operating loads, and the same material relatively flexible at higher strains, for example when the blades are folded in the stored condition. For example, the strain might be 10 percent at operating loads and 75 percent while folded, and the stress/strain curve has high modulus (e.g. 10000) at operating loads, and low modulus (e.g. 1000) at higher loads associated with folding. The stress-strain curve may have two approximately linear regions with a break point between the operating point and the folded point strains.

Figure 13:
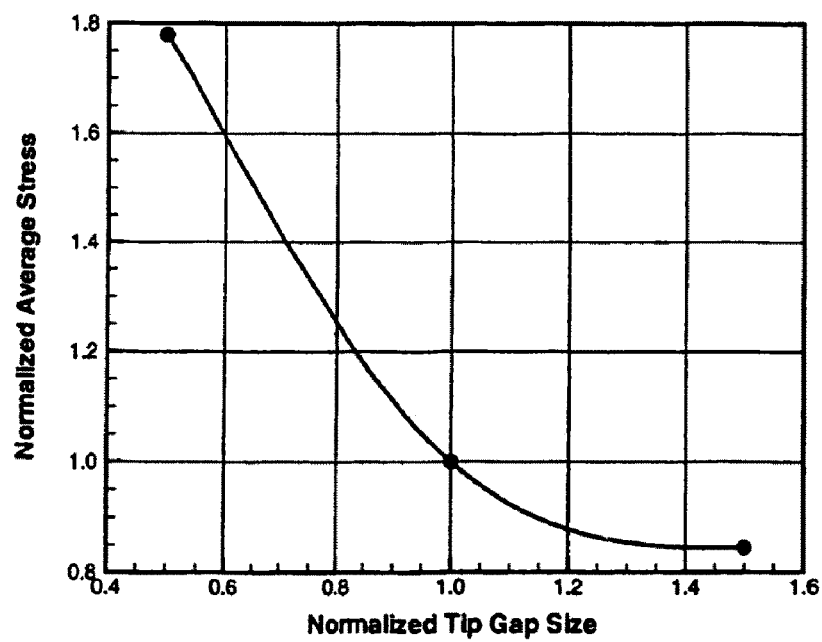
FIG. 13 shows normalized average fluid shearing stress as a function of tip gap sizes.

FIG. 13 illustrates optimization for fluid shear stress for an example impeller. The distal end of the impeller blade moves proximate to the interior surface of a cylindrical sleeve, the tip gap between the blade distal end and the inner diameter of the sleeve being approximately 10 to 50 percent of the maximum thickness of the distal end of the blade.

The curve is double normalized, the design point value being 1.0, the scale being read as a factor times the value of stress at the design point. For example, FIG. 13 illustrates that making the tip gap smaller makes the shear stress higher, whereas making the gap bigger reduces the stress by a smaller factor. Therefore, the fluid shear stress can be reduced without significantly impacting pumping efficiency.

Impellers according to embodiments of the present invention may be compressed and packaged into a storage sleeve, such as a metal tube, catheter, or other structure, for insertion into an object. For an object such as a living subject, the diameter of the storage sleeve can be approximately three to four millimeters, or less. Having inserted the device, the impeller can be deployed in situ into a geometry that may be approximately six to seven millimeters in diameter. The impeller then can be rotated using a flexible drive shaft coupled to a drive motor external to the subject. Impellers according to the present invention can be inserted in the stored state, then deployed into an expanded configuration (relative to the stored state) and are capable of pumping 4 liters per minute, for example, as a medical assist device. In a representative example of such a device, the impeller rotates at approximately 30,000 RPM. The impeller may comprise two or more airfoil shaped blades that form an axial flow pump. The impeller may be positioned using a guide wire and rotated using a flexible shaft. The guide wire may run within a hollow center of the flexible shaft, and the hollow center may also convey saline solution or other fluid for infusion, cooling, and/or lubrication purposes. The guide wire may be removed, if desired. Implantation into a living subject can be achieved through a cannula having a diameter of 3-4 mm, without surgical intervention. For medical implantation, a drive shaft comprising a metal braid, or a polymer or composite material braid, can be used, and the drive shaft diameter may be of the order 1½ to 2 millimeters, and may be hollow to allow a guide wire to pass through.

In further embodiments, the sleeve has expandable and non-expandable portions. The impeller is stored within the non-expandable portion for insertion. When the impeller is located at or near the desired location, the impeller is then urged out of the non-expandable portion of the sleeve into the expandable portion. The stored elastic energy within the flexible blades of the impeller induces self-deployment of the impeller, and also the expansion of the expandable portion of the sleeve. The expanded sleeve then may have the role of a fluid flow pipe, through which fluid flows when the impeller is rotated. The expandable sleeve may comprise a metal or polymer mesh, or woven fibers, and a smooth sheathing to provide a flexible, expandable tube.

An expandable sleeve may comprise a mesh formed from a flexible material, such as polymers, metals, or other material. In one example, the mesh is made from nitinol, a memory metal alloy. A thin sheet or cylinder of the metal, of a thickness on the order of a thousandth of an inch, is cut using a laser so as to leave a mesh structure. Alternatively, the mesh can be formed from a polymer. Other suitable materials for the mesh include other metals (such as alloys, including memory metal alloy), polymers, and the like. A coating, such an elastic coating, is then provided over the mesh. For example, an elastic polymer such as Estane™ can be used, or other polyurethane.

Hence, the expandable sleeve may comprise a mesh, such as a matrix of woven wires, or a machined metal cylinder with laser cut voids representing the spaces between wires, or another material that when deformed in one direction would elongate in the perpendicular direction. The mesh can then be covered with a thin film of elastane to form a fluid flow pipe through which the fluid flows. The mesh can be formed as a cylinder with flow entrance voids at the distal end and flow discharge voids at the proximal end, the proximal end being closer to the point of insertion into an object, such as a pipe or living subject. As the sleeve is shortened in length, for example using a guide wire, the cylinder expands to a greater diameter, allowing a greater flow rate. A hexagonal cell matrix design, or other design, can be used for the mesh. A coating (for example, biocompatible, corrosion resistant, or flow improving) can be applied to the sleeve, for example by solution casting.

The orientation of the mesh or woven fibers of the sleeve can be chosen to allow two stable configurations, stored and deployed. In one example, designed for subject implantation in the stored position, the expandable sleeve in the deployed configuration was approximately 20-30 cm long and the diameter was approximately 6-7 mm. This diameter allowed for higher fluid flow rate and reduced friction pressure losses. In the stored configuration, the expandable portion was elongated by approximately 30 percent relative to the deployed configuration, and the diameter was approximately 3 mm. The final portion (distal end) of the assembly comprises a second set of openings and plates, providing an inlet or opening for the influx of fluid to be pumped. The sleeve may also provide a guide wire attachment opening for fluid discharge. A short (such as 1 cm) section of the sleeve may contain linear elements (vanes) arranged about the central axis of the sleeve, through which fluid is discharged. The vanes may act as stationary stator blades and remove swirl velocity from the impeller discharge flow. The vanes may be manufactured with airfoil type cross-sections. Applications of an impeller deploying within an expandable sleeve include a collapsible fire hose with an integral booster pump, a collapsible propulsor, a biomedical pump for a biological fluid, and the like.

The impeller blade can be designed so as to minimize destruction of delicate particles (such as emulsion droplets, suspensions, biological structures such as cells, and the like) within a fluid. A CFD model was used to simulate the shear stresses experienced by particles passing through a simulated impeller. Time integrations of intermediate shear stresses experienced by the particles were used to provide an estimated probability of cell destruction in a biomedical application. A split blade design, in which there are a plurality of blade rows such as discussed above, reduces the residency time that cells remain in intermediate shear stress regions, allowing an advantageous reduction in cell or other particle destruction compared with conventional impeller designs.

Impeller blades may, for example, occupy as much as 95% of the compressed volume of the impeller when the impeller is in the stored state. The blades may be formed from a rubbery, elastic, or other resilient material that has sufficient resilience to expand when ejected from a sleeve. In other examples, the blades may be formed from other flexible polymers, an expandable foam optionally with a skin, or other compressible or deformable materials including metals.

Impellers according to embodiments of the present invention may have multiple separate sets of blades, rather than a long, continuous, spiral blade. Prior art impellers typically have a continuous long helical blade that is difficult to fold up against the hub. By splitting a long blade into two or three shorter sections, the blade can be more easily folded into a cylindrical volume or space and subsequently deployed when properly located. The number of blade rows can be one, two, three, four, five, or higher. The twist pitch angles may be variable.

One approach to impeller design provides a two blade impeller with blades exhibiting a significant degree of wrap around the central hub. However, the three-dimensional shape of the blades limits the degree to which they can be folded without deforming or breaking. By breaking a single blade row into two, three (or possibly more) rows of blades that exhibit minimum wrap around the hub, the blades have a more two-dimensional shape, allowing easier bending during the storage process. The combination of three or two blade rows can produce the same flow and pressure as a single blade row. An axial pump was designed with two blade rows, and CFD (computational fluid dynamics) analysis indicated that this pump design was adequate for use in a medical assist application. A model was constructed of a flexible polyurethane material and successfully folded into a metal sleeve.

Impellers can be used with flows of very small Reynolds number, for example, the pumping of relatively viscous fluids at low velocity or flow rate. Very small impeller pumps, on the order of 6 mm diameter, may be fabricated from a polymer and extracted from a precision mold. This allows production of impellers at very low cost. The use of polymer blades allows the pump impellers to be extracted from molds without becoming mold-locked, and allows the use of one-piece molds, instead of multi-part or split molds. This can be advantageous for pumping small quantities of bio-fluids. Impellers may be used for flows of typical Reynolds numbers as well. Impeller diameters can also be in the range of several inches to several feet.

Applications of the improved impeller designs described include pumps for chemical engineering, propellers for airborne or maritime vessels, water pumps, and the like. Improved impeller designs are useful for any application where an impeller is to be stored in a compact configuration. Impellers may be formed from metal sheets, plastic, and non-resilient materials, for example, in foldable configurations. Deployment may include the use of motors or other mechanical devices to unfold blades, automatic deployment induced by centrifugal forces, and the like. Examples of the present invention include a device locatable inside a subject so as to pump a fluid, the device being inserted into the subject in an insertion configuration having an insertion cross-section, the device operating inside the subject in an operating configuration having an operating cross-section, wherein the operating cross-section is greater than the insertion cross-section.

The operating diameter (of the largest circle swept out by the outer edge of the impeller blade as it rotates) may be over 50% greater than the insertion diameter of the impeller, and may be over 100% greater than the insertion diameter.

The invention is not restricted to the illustrative examples described above. Examples are not intended as limitations on the scope of the invention. Methods, apparatus, compositions, and the like described herein are exemplary and not intended as limitations on the scope of the invention. Changes therein and other uses will occur to those skilled in the art. The scope of the invention is defined by the scope of the claims.

Patents, patent applications, or publications mentioned in this specification are incorporated herein by reference to the same extent as if each individual document was specifically and individually indicated to be incorporated by reference.

The invention claimed is:

1. An apparatus for inducing motion of a fluid relative to the apparatus, the apparatus comprising:
    an impeller, including:
        a hub extending in a length direction; and
        a plurality of blades supported by the hub, each blade having a proximal end attached to the hub and a distal end;
        the blades being arranged in at least two blade rows arranged in series in the length direction of the hub;
        the impeller having a deployed configuration and a stored configuration, each blade in the deployed configuration of the impeller extending away from the hub, and at least one of the blades in the stored configuration of the impeller being compressed so as to move the distal end of the at least one blade towards the hub; and
    an expandable sleeve including a matrix and a film disposed around the matrix, at least part of the impeller being located within the sleeve.

2. The apparatus as claimed in claim 1, wherein each blade row includes at least two blades.

3. The apparatus as claimed in claim 1, wherein the distal end of at least one of the plurality of blades includes a winglet.

4. The apparatus as claimed in claim 1, wherein the distal end of each blade in at least one blade row includes a winglet.

5. The apparatus as claimed in claim 1, wherein the distal end of each of the plurality of blades includes a winglet.

6. The apparatus as claimed in claim 1, wherein the blades are formed integrally with the hub.

7. The apparatus as claimed in claim 1, wherein the impeller has a first radius in the deployed configuration and a radius in the stored configuration which is less than half the first radius.

8. The apparatus as claimed in claim 1, wherein the matrix is formed from a shape memory material.

9. The apparatus as claimed in claim 1, wherein the film includes an elastic polymer.

10. The apparatus as claimed in claim 1, wherein the expandable sleeve has a storage configuration and an expanded configuration, the sleeve in the storage configuration having a diameter less than about 4 mm.

11. The apparatus as claimed in claim 1, wherein the expandable sleeve has an inlet end and a discharge end, the sleeve including a plurality of vanes arranged at the discharge end.

12. The apparatus as claimed in claim 11, wherein each of the plurality of vanes has an airfoil-shaped cross-section.

13. An apparatus for inducing motion of a fluid relative to the apparatus, the apparatus comprising:
    an impeller, including:
        a hub extending in a length direction; and
        a plurality of blades supported by the hub, each blade having a proximal end attached to the hub and a distal end;
        the blades being arranged in at least two blade rows arranged in series in the length direction of the hub;
        the impeller having a deployed configuration, a stored configuration, and an operational configuration, each blade in the deployed configuration of the impeller extending away from the hub, at least one of the blades in the stored configuration of the impeller being compressed so as to move the distal end of the at least one blade towards the hub, and at least some of the blades in the operational configuration being deformed from the deployed configuration upon rotation of the impeller when in the deployed configuration;
    wherein the impeller in the operational configuration is operable to pump about 4 liters of fluid per minute.

14. The apparatus as claimed in claim 13, wherein the impeller has a first radius in the deployed configuration and a second radius in the stored configuration which is less than half the first radius.

15. The apparatus as claimed in claim 14, wherein the impeller has a third radius in the operational configuration, the second radius being less than half the third radius.

16. An apparatus for inducing motion of a fluid relative to the apparatus, the apparatus comprising:
    an elongated cannula having a proximal portion and a distal portion, the proximal portion including a conduit having a fixed diameter, and the distal portion including an expandable conduit having a diameter expandable to a diameter greater than the fixed diameter, the conduit having a substantially constant transverse width along its length when expanded;
    an impeller positioned in the elongated cannula and having a deployed configuration and a stored configuration, the impeller having substantially the same length in the deployed and stored configurations; and
    a drive shaft operably coupled with the impeller at a proximal end thereof.

17. The apparatus of claim 16, wherein the impeller is compressed in the stored configuration so as to move the radially outward portion of the impeller towards the drive shaft.

18. The apparatus of claim 16, wherein the impeller comprises an axially-extending hub and at least two blades supported by the hub, the at least two blades being at least partially axially offset from each other.

19. An apparatus for inducing motion of a fluid, comprising:
   a drive shaft configured to be operably coupled with a motor;
   an impeller having one or more impeller blades supported by and extending radially outward from an annular structure, the impeller having a blade region having a proximal end corresponding to the proximal end of the proximal-most impeller blade and a distal end corresponding to the distal end of the distal-most impeller blade, the annular structure being operably coupled with the drive shaft at a distal section of the drive shaft, wherein the impeller is configured to self-deploy into a deployed configuration from a compressed configuration; and
   a housing having an expandable section that encompasses the impeller, wherein the housing comprises a mesh, wherein openings of the mesh are closed by an elastic covering disposed in at least a portion of the expandable section;
   wherein a length between the proximal end and the distal end of the blade region is substantially the same when the impeller is in the deployed configuration and when the impeller is in the compressed configuration.

20. The apparatus of claim 19, wherein the housing is made of an elastic material such that, after forced compression, the impeller unfolds automatically.

21. The apparatus of claim 19, wherein the mesh of the housing is made of a flexible material.

22. The apparatus of claim 21, wherein the flexible material comprises at least one of nitinol and a polymer material.

23. The apparatus of claim 19, wherein the mesh of the housing is made of a flexible material.

24. The apparatus of claim 19, wherein the elastic covering of the pump housing comprises a polymer coating.

25. The apparatus of claim 19, wherein the polymer coating comprises polyurethane.

26. The apparatus of claim 19, further comprising an expandable outlet conduit disposed proximally of the impeller.

27. The apparatus of claim 19, wherein the drive shaft is at least partially housed within a sleeve.

* * * * *